United States Patent [19]

Deprez et al.

[11] Patent Number: 5,612,043
[45] Date of Patent: Mar. 18, 1997

[54] OIL-IN-WATER EMULSION CONTAINING A PERFLUOROPOLYETHER, COMPOSITION CONTAINING THE SAME, PREPARATION PROCESS AND USE IN COSMETICS AND DERMATOLOGY

[75] Inventors: Sabine Deprez, Morangis; Didier Candau, Bièvres, both of France

[73] Assignee: L'Oreal, Paris, France

[21] Appl. No.: 338,466

[22] PCT Filed: Mar. 17, 1994

[86] PCT No.: PCT/FR94/00295

§ 371 Date: Jan. 19, 1995

§ 102(e) Date: Jan. 19, 1995

[87] PCT Pub. No.: WO94/21233

PCT Pub. Date: Sep. 29, 1994

[30] Foreign Application Priority Data

Mar. 18, 1993 [FR] France ................... 93 03158

[51] Int. Cl.$^6$ ....................... A61K 7/00
[52] U.S. Cl. ............ 424/401; 424/70.7; 424/59; 252/312; 252/309; 514/845; 514/944
[58] Field of Search ................. 424/401, 70.7, 424/59; 252/312, 309; 514/845, 944

[56] References Cited

U.S. PATENT DOCUMENTS

| | | | |
|---|---|---|---|
| 4,803,067 | 2/1989 | Brunetta et al. | 424/63 |
| 4,975,468 | 12/1990 | Brunetta et al. | 252/308 |
| 4,990,283 | 2/1991 | Visca et al. | 252/309 |
| 5,183,589 | 2/1993 | Yiv | 514/759 |
| 5,306,498 | 4/1994 | Vesperini et al. | 424/401 |
| 5,330,681 | 7/1994 | Brunetta et al. | 252/312 |

FOREIGN PATENT DOCUMENTS

| | | |
|---|---|---|
| 0051526 | 5/1982 | European Pat. Off. . |
| 0390206 | 10/1990 | European Pat. Off. . |
| 0391637 | 10/1990 | European Pat. Off. . |
| 0494412 | 7/1992 | European Pat. Off. . |
| 60-034730 | 2/1985 | Japan . |

*Primary Examiner*—Margaret W. Glass
*Attorney, Agent, or Firm*—Jacobson, Price, Holman & Stern, PLLC

[57] ABSTRACT

The invention relates to an oil-in-water emulsion, characterized in that it contains at least:
  one perfluoropolyether,
  one fluoro surfactant, with the exception of any cationic fluoro surfactant,
  one co-emulsifying agent,
  one fatty alcohol,
  a gelled aqueous phase,
to a process for its preparation and to its use for the preparation of cosmetic compositions, as well as to the cosmetic compositions containing the same.

24 Claims, No Drawings

OIL-IN-WATER EMULSION CONTAINING A PERFLUOROPOLYETHER, COMPOSITION CONTAINING THE SAME, PREPARATION PROCESS AND USE IN COSMETICS AND DERMATOLOGY

The present invention relates to oil-in-water emulsions containing a perfluoropolyether, to their preparation, to cosmetic or dermatological compositions and to their use in the field of cosmetics and dermatology.

In the field of emulsions, those based on a liquid perfluoropolyether are known. They are, however, difficult to formulate. Indeed, perfluoropolyethers can only be made compatible with the usual cosmetic starting materials with difficulty: perfluoropolyethers are effectively insoluble in water and in many organic substances, apart from organic substances having a high fluorine content.

Numerous attempts have been made to overcome these difficulties. Thus, document EP-390206 describes an emulsion of liquid perfluoropolyethers in a hydrophilic medium where the hydrophilic phase consists essentially of a hydroxylated organic compound containing at least three hydroxyl units; the emulsion obtained then serves as a premix for the introduction of the perfluoropolyethers. This method is difficult to carry out insofar as it requires the production of a pre-emulsion into which the perfluoropolyether is introduced.

Moreover, document EP-494412 describes emulsions based on perfluoropolyethers and fatty substances; the stability thereof is provided by a polyol containing at least three hydroxyl functions, in an amount of greater than 10 %, and a surfactant which is soluble in the polyol. The difficulty therein also arises from the fact that the formulation is laborious to produce, because of the step for preparation of the pre-emulsion. Anhydrous or virtually anhydrous emulsions are prepared and water may then be added thereto.

Moreover, three-phase emulsions are described in particular in documents EP-360292, J63-107911 and EP-422984. The perfluoropolyether is, in these emulsions, dispersed in a water-in-oil or oil-in-water emulsion. Their preparation requires vigorous stirring, which allows the homogeneous dispersion of the perfluoropolyether(s) to be obtained. In these cases, suspension of the perfluoropolyethers in the three-phase system results, not in a thermodynamic phenomenon, but in a mechanical phenomenon; the stability of these systems is low insofar as the perfluoropolyether droplets, which are visible under a microscope, have a tendency to coalesce.

The non-homogeneous distribution of the oily perfluoropolyethers in the cosmetic preparations quite often results in a reduction in the performance of the oily perfluoropolyethers.

The Applicant has demonstrated a system which allows cosmetic emulsions containing oils of perfluoropolyether type to be stabilized in a simple manner, without involving a step for preparation of a pre-emulsion. They in fact contain, in one step, a certain amount of water when they are prepared. These emulsions according to the invention make it possible to use perfluoropolyethers, which are very useful in cosmetics for their protective film-forming and moisturizing effect, and in an effective minimum percentage, without the standard problems of homogeneity and stability arising, which problems have hitherto arisen when it has been desired to prepare a perfluoro oil/water emulsion directly.

The present invention relates to an oil-in-water emulsion containing at least one perfluoropolyether, a fluoro surfactant with the exclusion of cationic fluoro surfactants, a co-emulsifying agent, a fatty alcohol and a gelled aqueous phase.

The stable emulsion of perfluoropolyethers in water may be produced according to the invention by the stabilization which is produced by the presence of the four constituents, acting in synergy.

The Applicant has thus demonstrated that formulations prepared for comparison and using, besides the perfluoropolyether and water, only one, two or three of the components from among the gelling agent, the fluoro surfactant, the co-emulsifying agent and the alcohol did not lead to a fine and stable emulsion.

The emulsifying system according to the invention enables large amounts of perfluoropolyethers to be incorporated, relative to the amounts usually incorporated into the known compositions of greater or lesser stability, while at the same time remaining stable and homogeneous, and these emulsions are obtained directly.

Moreover, these emulsions contain good sensory properties associated with the presence of perfluoropolyethers: in fact, they are comfortable, very easy to apply and lead to the formation of a very thin film which is very soft and uniformand has good protection and staying properties.

According to the invention, the fluoro surfactant is preferably used in amounts ranging from 0.5 to 10% by weight relative to the total weight of the emulsion, and preferably from 1 to 3% by weight.

According to the invention, the co-emulsifying agent is preferably a hydrocarbon; it is used in percentages ranging from 0.1 to 5% by weight relative to the total weight of the composition, and preferably from 0.1 to 0.3 %.

The fatty alcohol is used, according to the invention, in an amount ranging from 0.5 to 10% by weight, and preferably from 1 to 3% by weight, relative to the total weight of the composition.

The gelled aqueous phase is used, according to the invention, in an amount which may range from 10 to 90% by weight relative to the total weight of the emulsion.

The perfluoropolyethers or mixtures thereof are themselves used in amounts ranging from 0.5 to 50% by weight relative to the total weight of the composition, and preferably from 5 to 20% by weight.

According to the invention, the liquid perfluoropolyethers used in the emulsions may be of the functionalized type or of the non-functionalized type.

Among the non-functionalized perfluoropolyethers, there may in particular be mentioned the compounds of formula (I):

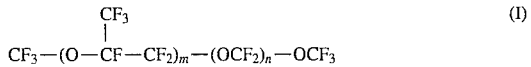

in which m/n=5 to 40 and m and n are chosen such that the average molecular weight i s higher than 500 and preferably between 1000 and 10,000.

Among these non- functionalized perfluoropolyethers, there may be mentioned those which are sold under the names "FOMBLIN HC", "FOMBLIN Y", "FOMBLIN HCR" (molecular weight: 6250) , "FOMBLIN HC-04" (molecular weight: 1500), "FOMBLIN HC-25" (molecular weight: 3200) and "GALDEN" by the company MONTEFLUOS.

There may also be mentioned the compounds of following formula (II):

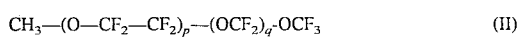

in which p/q is from 0.5 to 1.5, the average molecular weight being higher than 500 and preferably between 1000 and 10,000.

Among these compounds, there may be mentioned the compound sold under the name "FOMBLIN Z" by the company MONTEFLUOS.

There may also be mentioned the compounds of following formula (III):

$$F-(CF-CF_2O)_n-CF_2-CF_3 \quad\quad (III)$$
$$\quad\; |$$
$$CF_3$$

in which n is an integer from 4 to 500.

Among these compounds, there may be mentioned the compound sold under the name "KRYTOX" by the company DU PONT DE NEMOURS.

Finally, there may be mentioned the compounds having the following formula (IV):

$$CF_3-CF-O-(CF_2-CF-O)_m-C_3F_7 \quad\quad (IV)$$
$$\quad\quad\quad\quad\quad\quad\quad\quad |$$
$$\quad\quad\quad\quad\quad\quad\quad\quad CF_3$$
$$CF_3-CF-O-(CF_2-CF-O)_n-C_3F_7$$
$$\quad\quad\quad\quad\quad\quad\quad\quad |$$
$$\quad\quad\quad\quad\quad\quad\quad\quad CF_3$$

in which n and m are integers from 0 to 3

Among these compounds, there may be mentioned the compounds sold under the name "HOSTINERT" by the company HOECHST.

Among the functionalized perfluoropolyethers, there may be mentioned the compounds having the following formula:

$$RCF_2-(O-CF_2CF_2)_p-(OCF_2)_q-OCF_2R \quad\quad (V)$$

in which:

p/q is from 0.5 to 1.5, and R represents a residue —COOCH$_3$, —CH$_2$OH, —CH$_2$O—CH$_2$—CHOHCH$_2$OH or —CH$_2$—(OCH$_2$—CH$_2$)$_t$—OH where t is 1 or 2, the average molecular weight being higher than 500 and preferably between 1000 and 10,000

Among these functionalized perfluoropolyethers, there may be mentioned the compounds sold under the names "FOMBLIN Z-DOL" (R=—CH$_2$OH), "FOMBLIN Z TETRAOL" (R =CH$_2$O—CH$_2$—CHOHCH$_2$OH) and "FOMBLIN Z-DOL-TX" [(R=CH$_2$(OCH$_2$CH$_2$)$_t$OH, t being 1 or 2)]by the company MONTEFLUOS.

By way of fluoro surfactants, with the exception of cationic fluoro surfactants, it is possible, according to the invention, to use:

fluoroalkylpolyglycerolated surfactants of formula (VI):

$$R_f-(CH_2)_m-S-G_n-H \quad\quad (VI)$$

in which:

$R_f$ denotes a linear or branched $C_6$ to $C_{20}$ perfluoroalkyl radical or a mixture of linear or branched $C_4$ to $C_{20}$ perfluoroalkyl radicals;

m represents 0, 1 or 2;

n represents a statistical value or an integer between 1 and 10;

G represents a Knit chosen from:

—CH$_2$—CH—CH$_2$—O—, —CH—CH$_2$—O—,
$\quad\quad\;\;\;|\quad\quad\quad\quad\quad\quad\quad\;\;\;|$
$\quad\quad\;\;\;O\quad\quad\quad\quad\quad\quad\quad\;CH_2$
$\quad\quad\;\;\;|\quad\quad\quad\quad\quad\quad\quad\quad|$
$\quad\quad\quad\quad\quad\quad\quad\quad\quad\quad\quad\;O$
$\quad\quad\quad\quad\quad\quad\quad\quad\quad\quad\quad\;|$ -continued
—CH$_2$—CH—CH$_2$—O—, —CH—CH$_2$—O—,
$\quad\quad\;\;\;|\quad\quad\quad\quad\quad\quad\quad\;|$
$\quad\quad\;\;\;OH\quad\quad\quad\quad\quad\quad CH_2OH$ or —CH$_2$—CH—O—,
$\quad\quad\quad\;|$
$\quad\quad\quad CH_2OH$ it being possible for each of the oxygen atoms to be linked to a hydrogen atom or to another unit G; in the formula (VI), R$_f$ preferably denotes a linear or branched C$_6$ to C$_{14}$ perfluoroalkyl radical and m is 2; or oxyethylenated or oxypropylenated perfluoroalkyls of formula (VII):

$$RF-(CH_2)_m-X-\left[\left(\begin{array}{c}CH\\|\\R\end{array}\right)_r -CH_2O\right]_q-H \quad\quad (VII)$$

where

RF is a perfluoroalkyl group $C_nF_{2n+1}$ where n is between 3 and 20;

m=0, 1 or 2, preferably 2;

q=1 to 10, preferably 2;

R is a methyl group or hydrogen;

r=1 when R=CH$_3$ and r =1 or 2 when R =H;

X is an oxygen or sulfur atom.

It is especially possible to use the compounds sold under the name "ZONYL FSN" and "ZONYL FSN 100" by the company DU PONT.

The compounds of formula (VI) are described in French Patent Application No. 92-09404 filed on 29 Jul. 1992.

These compounds of formula (VI) may be prepared by carrying out the reaction of a fluoromercaptan of formula (VIII):

$$R_f-(CH_2)_m-S-H \quad\quad (VIII),$$

in which $R_f$ and m have the same meanings as in the formula (VI), in the presence of an active amount of basic catalyst, a) by condensation with n moles
   of glycidol, or
   of a compound containing an epoxide function which is capable, after reaction, of regenerating an alcohol function,
   optionally followed by a neutralization; or b) on glycidyl isopropylideneglyceryl ether, when n, which is an integer, is equal to 2 or to a multiple of 2, optionally followed by a hydrolysis; or c) on glycidyl diisopropylidenetriglyceryl ether, when n is an integer equal to 4,
   optionally followed by a hydrolysis.

Certain cationic fluoro surfactants are not suitable. In particular, certain quaternary ammonium surfactants, such as the compound known under the name "LODYNE S106B" from CIBA, are not suitable.

Among the hydrocarbon co-emulsifying agents which may be used in the emulsions according to the invention, there may be mentioned:

a) ethylene oxide-propylene oxide copolymers and in particular those sold under the name "SYMPERONIC" by the company ICI, which have the general formula:

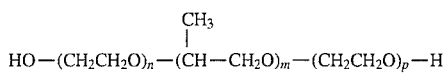

where m, n and p have values of from 2 to 100, and more particularly SYMPERONIC PE/F68 where n=75, m=30 and p=75; and b) C₄–C₂₀ polyoxyethylenated and/or polyoxypropylenated ethers, for example PPG-26-Butheth-26 from the company WITCO or Steareth-100 (Brij 700) from the company ICI.

As fatty alcohols which may be used according to the invention, there may be mentioned all the alcohols containing a hydrocarbon chain of between $C_{12}$ and $C_{22}$, and in particular cetyl alcohol, lauryl glycol marketed in particular by the company CHIMEX under the name "MEXANYL GU", or octyldodecanol sold under the name "ISOFOL 20F" by the company CONDEA.

As regards the gelled aqueous phase, the content of gelling agent depends on the nature of the gelling agent and on the starting material used. Thus, the amount of gelling agent may range from 0.1 to 60% by weight relative to the total weight of the composition. It is in fact possible to use, for example, 0.5 % of a powder and up to approximately 60 % of an aqueous gel whose active material content is usually much lower.

Among the aqueous gelling agents according to the invention, there may be mentioned:

modified celluloses such as hydroxyethylcellulose, methylcellulose, hydroxypropylcellulose and carboxymethylcellulose. Among these, there may in particular be mentioned the gums sold under the name "CELLOSIZE QP 4400H" by the company AMERCHOL;

carob gum, guar gum, quaternized guar gum sold under the name "JAGUAR C-13-S" by the company MEYHALL, hydroxypropylguar gum and xanthan gum;

crosslinked polyacrylic acids such as the CARBOPOLS from the company GOODRICH;

polyglyceryl (meth) acrylate polymers, sold under the names "HISPAGEL" or "LUBRAGEL" by the companies HISPANO QUIMICA or GUARDIAN;

polyvinylpyrrolidone and polyvinyl alcohol;

crosslinked polymers of acrylamide and ammonium acrylate, sold under the names "PAS 5161" or "BOZEPOL C" by the company HOECHST, crosslinked polymers of acrylamide and partially or totally neutralized 2-acrylamido2-methylpropanesulfonic acid, sold under the reference "SEPIGEL 305" by the company SEPPIC, crosslinked polymers of acrylamide and methacryloyloxyethyltrimethylammonium chloride, sold under the reference "SALCARE SC92" by the company ALLIED COLLOIDS; or alternatively crosslinked homopolymers of methacryloyloxyethyltrimethylammoniumchloride, sold under the reference "SALCARE SC95" by the company ALLIED COLLOIDS.

According to the invention, the fatty phase of the emulsion contains the perfluoropolyethers mentioned above and the fatty alcohol(s), but it may additionally contain, in emulsified form in the aqueous phase, other oils which are usually employed in cosmetology. Thus, the fatty phase may additionally contain hydrocarbon oils and waxes such as squalane, liquid paraffins, vaseline, parleam oil and lanolin; fatty acid esters such as 2-ethylhexyl palmitate, isopropyl myristate or 2-cetylethyl hexanoate; triglycerides such as jojoba oil, sesame oil, avocado oil or apricot oil, or synthetic triglycerides of $C_8$–$C_{18}$ fatty acids; inorganic waxes such as ozokerite, paraffins or ceresin; plant or animal waxes such as carnauba wax or beeswax; synthetic waxes such as polyethylene waxes; silicones such as cyclic dimethylpolysiloxanes, dimethylpolysiloxanes of low and/or of high viscosity, silicone gums, organopolysiloxanes such as phenylmethylpolysiloxanes, alkylmethylpolysiloxanes and alkoxymethylpolysiloxanes, silicones containing functional groups such as alcohol or amine or thiol functions, and fluorosilicones.

Among the fluorosilicones, there may be mentioned those having the following formula:

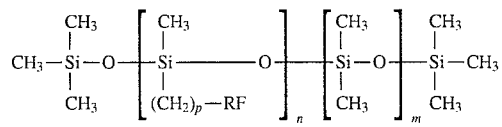

which:

n is an integer from 1 to 300, m is an integer from 0 to 150, p is an integer from 0 to 5, and RF is a perfluoroalkyl radical having from 1 to 8 carbon atoms.

Among the fluorosilicones, there may be mentioned those sold by the company SHIN-ETSU under the names "FL-100", "X 22819", "X 22820", "X 22821" and "X 22822", as well as those sold by the company DOW CORNING under the name "FS 1265" and those sold by the company GENERAL ELECTRIC under the name "FF 150".

It is also possible to use perfluoro oils such as, for example, perfluoroalkanes, perfluorocycloalkanes, perfluoro(alkylcycloalkanes), aromatic perfluorohydrocarbons or perfluorohydrocarbons containing at least one hetero atom, such as tertiary amines and saturated heterocyclic compounds.

The fatty phase of the emulsions according to the invention may also contain screening agents, vitamins, hormones, cosmetic active agents, antioxidants, preserving agents, dyes, fragrances and lipid-soluble sunscreen agents.

This fatty phase constitutes the phase which is emulsified in the aqueous phase.

The gelled aqueous phase may additionally contain water, fluoro surfactant, the hydrocarbon co-emulsifying agent as well as other constituents which are usually used in the cosmetics field.

By way of additional constituents which may be incorporated into the aqueous phase, there may be mentioned polyols such as propylene glycol, 1,3-butylene glycol, glycerol and polyglycerol, sorbitol, glucose or alternatively sucrose; active agents such as hyaluronic acid, sodium hyaluronate, sodium pyroglutamate, magnesium gluconate, trace elements and biological derivatives; amino acids, dyes or sunscreen agents which are watersoluble.

There may also be m. entioned, by way of additional constituents:

plant powders such as corn starch, wheat starch or rice starch, inorganic powders such as talc, kaolin, mica, silica, silicates, alumina, zeolites, hydroxyapatite, sericite, titanium dioxide, titanium micas, zinc oxide, barium sulfate, iron oxides, manganese violet, chromium oxide, ultramarine blue and bismuth oxychloride or alternatively boron nitride, metal powders such as aluminum powder, organic powders such as nylon powders, polyamide powders, polyester powders, cellulose powders, polyethylene powders, polypropylene powders, polystyrene powders and polytetrafluoroethylene powders, organometallic pigments combining zirconium, barium or aluminum with organic dyes.

When pulverulent products such as those mentioned above are used, they may optionally be coated with fatty acid metal salts, amino acids, lecithin, collagen, polyethylene, silicone-containing compounds, fluoro compounds or fluorosilicone-containing compounds.

Thus, the present invention relates to a process for the preparation of the oil-in-water emulsions according to the invention, characterized in that:

the fluoro surfactant and the hydrocarbon co-emulsifying agent are dispersed in the aqueous phase, the aqueous gelling agent is added with vigorous stirring, the perfluoropolyether(s), the fatty alcohol and the optional adjuvants of the fatty phase are heated, and the fatty phase is incorporated into the aqueous phase with vigorous stirring.

In order to prepare the emulsions according to the invention, the fluoro surfactant and the hydrocarbon co-emulsifying agent are dispersed in water at 80° C., for example, using a high-shear mixer of "polytron" type.

The aqueous gelling agent is then added with vigorous stirring and all of the ingredients of the fatty phase including the perfluoropolyether(s), are heated to 80° C. The fatty phase is incorporated into the aqueous phase with vigorous stirring, like a standard oil-in-water emulsion.

The emulsion is then gradually cooled to room temperature while maintaining the stirring.

The emulsions thus obtained are stable for several months over a wide range of temperatures, between +4° C. and 45° C., and are resistant in the centrifugation test of 4000 revolutions/minute for 1 hour.

The emulsions prepared according to the invention may, at room temperature, assume various physical aspects, associated in particular with the nature of the constituents present in each of the phases and with the respective proportions of these phases. It is thus possible to obtain very different viscosity results, ranging from the very fluid to the least fluid, by acting upon the percentage of the aqueous phase relative to the fatty phase and/or alternatively by selecting viscosifying or structuring constituents in each of the phases.

In view of the good sensory properties of the emulsions produced, they find a host of applications in the cosmetics field and enable white products and colored products to be obtained.

Thus, the present invention relates to the use of the emulsions of the invention for the preparation of cosmetic or dermatological compositions.

It also relates to the cosmetic or dermatological compositions containing at least one emulsion of the invention.

The emulsions according to the invention may thus be provided in compositions in the form of a milk, a white cream, a care cream or an antisun cream, a tinted cream, a foundation or a mascara.

Processes for the cosmetic treatment of the skin and of the dermoskeleton may be carried out by application of the emulsions and/or compositions of the invention.

Other advantages and characteristics of the invention will appear on reading the examples below.

EXAMPLE FOR THE PREPARATION OF A FLUORO SURFACTANT

Example A

Fluoro surfactant of formula:

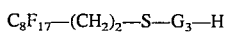

G representing a unit chosen from:

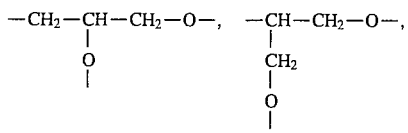

or

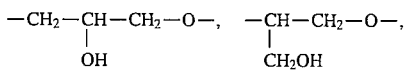

it being possible for each of the oxygen atoms to be linked to a hydrogen atom or to another unit G.

This compound is prepared according to the following procedure:

108 g (0,225 mol) of 2-F-octylethanethiol are introduced into a reactor under inert atmosphere. 1.26 g of potassium tert-butoxide (11.25 meq) are introduced with stirring and at a temperature of 25° C. The temperature is brought to between 50° and 60° C. and the system is placed under a vacuum of 4000 Pa in order to remove the tert-butanol. The temperature rise is monitored. When it reaches 80° C., 16.65 g of glycidol (0.225 mol) are added over 30 minutes, while maintaining a temperature in the region of 80° C. The reaction medium becomes pasty. In order to liquefy the mixture, 59 g of xylene are added over 15 minutes. The heating is pursued until the temperature reaches 130° C. 33.3 g of glycidol (0.45 mol) are added dropwise over 75 minutes at this temperature. At the end of the addition, the temperature is maintained at 130° C. for 15 minutes. The temperature is again raised to 155° C. and the xylene is removed by distillation at atmospheric pressure.

After 15 minutes at 155° C., the medium is neutralized by 11.5 ml of 1N HCl. Some frothing occurs, then the mixture becomes clear and the temperature falls to 135° C. At this temperature, the product is left for approximately 15 minutes at 4000 Pa and then solidifies at room temperature.

157 g of product are obtained.

Melting point: 64 ° C.

|  | ELEMENTAL ANALYSIS | | | |
| --- | --- | --- | --- | --- |
|  | % C | % H | % S | % F |
| Calculated | 32.48 | 3.27 | 4.56 | 46.01 |
| Found | 32.47 | 3.27 | 4.28 | 46.16 |

EXAMPLES OF OIL-IN-WATER EMULSIONS

Example 1

| Care cream | |
| --- | --- |
| Polyglyceryl acrylate sold under the name "HISPAGEL-100" by the company HISPANO QUIMICA | 56.14 g |
| Oxyethylenated polyfluoroalcohol sold under the name "ZONYL FSN 100" by the company DU PONT DE NEMOURS | 2.4 g |
| Ethylene oxide/propylene oxide condensate sold under the name "SYMPERONIC PE/F68" by the company ICI | 0.26 g |

-continued

| Care cream | |
|---|---|
| Cetyl alcohol sold under the name "SIPOL C16" by the company HENKEL | 3 g |
| Perfluoropolyethers sold under the name "FOMBLIN-HCR" by the company MONTEFLUOS | 15.4 g |
| Apricot oil | 5 g |
| Sesame oil | 1.5 g |
| Caprylic/capric triglyceride sold under the name "MIGLYOL 812" by the company HULS | 1.5 g |
| Water and preserving agents | 14.8 g |

Example 2

| Care cream | |
|---|---|
| Polyglyceryl acrylate sold under the name "HISPAGEL-100" by the company HISPANO QUIMICA | 56.14 g |
| Fluoro surfactant of Example A | 2.4 g |
| Butyl polyoxyproplylenated polyoxyethylenated ether sold under the name "WITCONOL APEB" by the company WITCO | 0.26 g |
| Cetyl alcohol sold under the name "SIPOL C16" by the company HENKEL | 3 g |
| Perfluoropolyether sold under the name "FOMBLIN-HCR" by the company MONTEFLUOS | 15.4 g |
| Water and preserving agents | 22.8 g |

Example 3

| Care cream | |
|---|---|
| Polyglyceryl acrylate sold under the name "HISPAGEL-100" by the company HISPANO QUIMICA | 56.14 g |
| Fluoro surfactant of Example A | 2.4 g |
| Ethylene oxide/propylene oxide condensate sold under the name "SYMPERONIC PE/F68" by the company ICI | 0.26 g |
| Cetyl alcohol sold under the name "SIPOL C16" by the company HENKEL | 3 g |
| Hexafluoropropylene epoxide homopolymer sold under the name "KRYTOX 143 AC" by the company DU PONT DE NEMOURS | 15.4 g |
| Water and preserving agents | 22.8 g |

Example 4

| Care cream | |
|---|---|
| Carboxyvinyl polymer sold under the name "SYNTHALEN K" by the company SIGMA | 0.5 g |
| Fluoro surfactant of Example A | 2.4 g |
| Ethylene oxide/propylene oxide condensate sold under the name "SYMPERONIC PE/F68" by the company ICI | 0.26 g |
| Cetyl alcohol sold under the name "SIPOL C16" by the company HENKEL | 3 g |
| Perfluoropolyether sold under the name "FOMBLIN-HC" by the company MONTEFLUOS | 15.4 g |
| Triethanolamine | 0.5 g |

-continued

| Care cream | |
|---|---|
| Glycerine | 5 g |
| Water and preserving agents | 72.94 g |

Example 5

| Care cream | |
|---|---|
| Polyglyceryl methacrylate sold under the name "LUBRAGEL" by the company GUARDIAN | 56.14 g |
| Fluoro surfactant of Example A | 2.4 g |
| Ethylene oxide/propylene oxide condensate sold under the name "STEARETH 100" by the company ICI | 0.26 g |
| Dodecanediol sold under the name "MEXANYL GU" by the company CHIMEX | 3 g |
| Perfluoropolyether sold under the name "FOMBLIN-HCR" by the company MONTEFLUOS | 15.4 g |
| Water and preserving agents | 22.8 g |

Example 6

| Foundation | |
|---|---|
| Polyglyceryl acrylate sold under the name "HISPAGEL-100" by the company HISPANO QUIMICA | 53.14 g |
| Fluoro surfactant of Example A | 2.4 g |
| Ethylene oxide/propylene oxide condensate sold under the name "SYMPERONIC PE/F68" by the company ICI | 0.26 g |
| Cetyl alcohol sold under the name "SIPOL C16" by the company HENKEL | 3 g |
| Perfluoropolyether sold under the name "GALDEN D03" by the company MONTEFLUOS | 15.4 g |
| Apricot oil | 5 g |
| Sesame oil | 1.5 g |
| Caprylic/capric triglyceride sold under the name "MIGLYOL 812" by the company HULS | 1.5 g |
| Titanium oxide | 4.8 g |
| Black pigment sold under the name "SICOMET Black" by the company BASF | 0.22 g |
| Yellow pigment sold under the name "SICOMET Yellow-10" by the company BASF | 4.43 g |
| Red pigment sold under the name "SICOMET Red" by the company BASF | 0.55 g |
| Water and preserving agents | 7.8 g |

Example 7

| Milk | |
|---|---|
| Phase A | |
| Polyglyceryl methacrylate sold under the name "LUBRAGEL" by the company GUARDIAN | 28.07 g |
| Fluoro surfactant of Example A | 1.2 g |
| Ethylene oxide/propylene oxide condensate sold under the name "SYMPERONIC PE/F68" by the company ICI | 0.13 g |
| Water | 8.4 g |

Example 8

Milk

Phase B

| | |
|---|---|
| Cetyl alcohol sold under the name "SIPOL C16" by the company HENKEL | 0.5 g |
| Perfluoropolyether sold under the name "FOMBLIN-HC" by the company MONTEFLUOS | 7.7 g |
| Apricot oil | 2.5 g |
| Sesame oil | 0.75 g |
| Caprylic/capric triglyceride sold under the name "MIGLYOL 812" by the company HULS | 0.75 g |

Phase C

| | |
|---|---|
| Water | 47.5 g |
| Polyglycerolated dodecanediol sold under the name "CHIMEXANE NF" by the company CHIMEX | 2.5 g |

In order to prepare the milk, phase B is poured into phase A, and phase C is then added thereto.

Example 8

Care cream

| | |
|---|---|
| Fluoro surfactant of Example A | 10 g |
| Ethylene oxide/propylene oxide condensate sold under the name "SYMPERONIC PE/F68" by the company ICI | 1 g |
| Methylparaben | 0.2 g |
| Water | 17.6 g |
| Polyglyceryl acrylate sold under the name "HISPAGEL 100" by the company HISPANO QUIMICA | 40 g |
| Cetyl alcohol | 1 g |
| Perfluoropolyether sold under the name "FOMBLIN-HCR" by the company MONTEFLUOS | 30 g |
| Propylparaben | 0.2 g |

A beige-colored cream is obtained as a fine emulsion.

Example 9

Care cream

| | |
|---|---|
| Fluoro surfactant of Example A | 2.5 g |
| Ethylene oxide/propylene oxide condensate sold under the name "SYMPERONIC PE/F68" by the company ICI | 0.26 g |
| Methylparaben | 0.2 g |
| Water | 20 g |
| Polyglyceryl acrylate sold under the name "HISPAGEL 100" by the company HISPANO QUIMICA | 55 g |
| Cetyl alcohol | 1 g |
| Perfluoropolyether sold under the name "FOMBLIN-HCR" by the company MONTEFLUOS | 1 g |
| Apricot oil | 10 g |
| Sesame oil | 4.92 g |
| Capric/caprylic acid triglycerides sold under the name "MIGLYOL 812" by the company DYNAMIT NOBEL | 4.92 g |
| Propylparaben | 0.2 g |

A white cream is obtained as a very fine emulsion.

Example 10

Care cream

| | |
|---|---|
| Fluoro surfactant of Example A | 10 g |
| Ethylene oxide/propylene oxide condensate sold under the name "SYMPERONIC PE/F68" by the company ICI | 1 g |
| Preserving agents | 0.4 g |
| Water | 16.6 g |
| Polyglyceryl acrylate sold under the name "HISPAGEL 100" by the company HISPANO QUIMICA | 56 g |
| Cetyl alcohol | 1 g |
| Perfluoropolyether sold under the name "FOMBLIN-HCR" by the company MONTEFLUOS | 15 g |

A beige-colored cream is obtained as a fine emulsion.

We claim:

1. Oil-in-water emulsion, comprising at least:
   one perfluoropolyether,
   one fluoro surfactant, with the exception of any cationic fluoro surfactant,
   one co-emulsifying agent,
   one fatty alcohol, and
   a gelled aqueous phase.

2. Emulsion according to claim 1, which contains from 0.5 to 10% by weight of at least one fluoro surfactant relative to the total weight of the emulsion.

3. Emulsion of claim 2, which contains from 1 to 3% by weight of at least one fluoro surfactant relative to the total weight of the emulsion.

4. Emulsion according to claim 1, which contains from 0.1 to 5% by weight relative to the total weight of the emulsion of at least one hydrocarbon co-emulsifying agent.

5. Emulsion of claim 4 which contains 0.1 to 0.3% by weight relative to the total weight of the emulsion of at least one hydrocarbon co-emulsifying agent.

6. Emulsion according to one of claim 1, which contains from 0.5 to 10% by weight relative to the total weight of the emulsion of at least one fatty alcohol.

7. Emulsion of claim 6, which contains from 1 to 3% by weight relative to the total weight of the emulsion of at least one fatty alcohol.

8. Emulsion according to claim 1, which contains from 0.5 to 50% by weight relative to the total weight of the emulsion of at least one perfluoropolyether.

9. Emulsion according to claim 8, which contains from 5 to 20% by weight relative to the total weight of the emulsion of at least one perfluoropolyether.

10. Emulsion according to one of claim 1, which contains from 10 to 90% by weight of gelled aqueous phase relative to the total weight of the emulsion.

11. Emulsion according to one of claim 1 wherein the perfluoropolyethers are selected from the group consisting of:

compounds of formula (I):

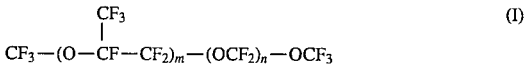

$$CF_3-(O-CF(CF_3)-CF_2)_m-(OCF_2)_n-OCF_3 \quad (I)$$

in which m/n=5 to 40, the average molecular weight being higher than 500 compounds of formula (II):

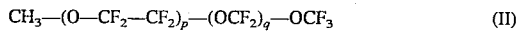

$$CH_3-(O-CF_2-CF_2)_p-(OCF_2)_q-OCF_3 \quad (II)$$

in which p/q is from 0.5 to 1.5, the average molecular weight being higher than 500, compounds of formula (III):

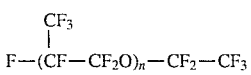  (III)

in which n is an integer from 4 to 500,
compounds of formula (IV):

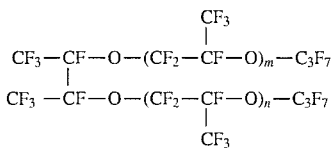  (IV)

in which n and m are integers from 0 to 3, and
compounds of formula (V):

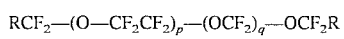  (V)

in which:
p/q is from 0.5 to 1.5, and
R represents a residue —COOCH$_3$, —CH$_2$OH, —CH$_2$O—CH$_2$—CHOHCH$_2$OH or —CH$_2$—(OCH$_2$—CH $_2$)$_t$—OH where t is 1 or 2, the average molecular weight being higher than 500.

12. Emulsion according to claim 11, wherein the average molecular weight of the compounds of formula (I), (II) and (V) is between 1000 and 10,000.

13. Emulsion according to claim 1, wherein the co-emulsifying agent is a compound selected from the group consisting of C$_4$–C$_{20}$ polyoxyethylenated and polyoxypropylenated ethers containing a hydrocarbon chain and ethylene oxide-propylene oxide copolymers.

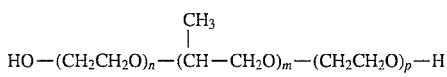

14. Emulsion according to claim 13, which contains compounds of formula:

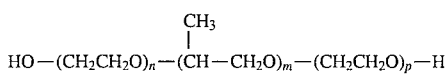

where m, n and p have values of from 2 to 100.

15. Emulsion according to claim 1, wherein the fluoro surfactants are selected from the group consisting of compounds of formula:

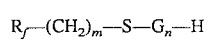  (VI)

in which:
R$_r$ denotes a linear or branched C$_6$ to C$_{20}$ perfluoroalkyl radical or a mixture of linear or branched C$_4$ to C$_{20}$ perfluoroalkyl radicals;
m represents 0, 1 or 2;
n represents a statistical value between 1 and 10 or an integer between 1 and 10;
G represents a unit selected from the group consisting of:

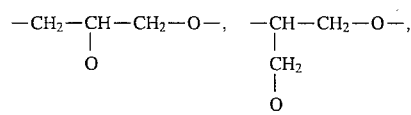

-continued

—CH$_2$—CH—CH$_2$—O—,  —CH—CH$_2$—O—,
      |                            |
      OH                    CH$_2$OH and  —CH$_2$—CH—O—,
              |
              CH$_2$OH each of the oxygen atoms being linked to a hydrogen atom or to another unit G, and
compounds of formula

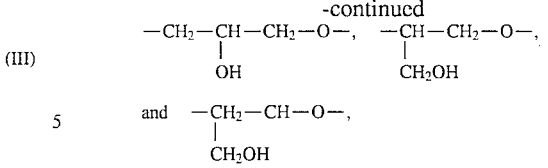  (VII)

where
RF is a perfluoroalkyl group C$_n$F$_{2n+1}$ where n is between 3 and 20;
m=0, 1 or 2;
q=1 to 10[,preferably 2];
R is a methyl group or hydrogen;
r=1 when R=CH$_3$;
r=1 or 2 when R=H; and
X is an oxygen or sulfur atom.

16. Emulsion according to claim 15, wherein in formula (VII) q=2.

17. Emulsion according to claim 1, wherein the gelled aqueous phase contains gelling agents selected from the group consisting of modified celluloses, carob gum, quaternized and non-quaternized guar gum, xanthan gum, hydroxypropyl guar gum, crosslinked polyacrylic acids, polyglyceryl (meth)acrylate polymers, polyvinylpyrrolidone, polyvinyl alcohol, crosslinked polymers of acrylamide and ammonium acrylate, crosslinked polymers of acrylamide and 2-acryl-amido-2-methylpropanesulfonic acid, crosslinked polymers of acrylamide and methacryloyloxyethyltrimethylammonium chloride, and crosslinked homopolymers of methacryloyloxyethyltrimethylammonium chloride.

18. Emulsion according to claim 17, wherein the modified celluloses are hydroxyethylcellulose, methylcellulose, hydroxypropylcellulose and carboxymethylcellulose.

19. Emulsion according to claim 1, wherein the fatty alcohols are selected from the group consisting of alcohols with a C$_{12}$–C$_{22}$ hydrocarbon chain.

20. Emulsion according to claim 19, wherein the fatty alcohols are cetyl alcohol, lauryl glycol and octldodecanol.

21. Emulsion according to claim 1, which contains the perfluoropolyethers and the fatty alcohol in a fatty phase, the fatty phase further containing a member selected from the group consisting of other oils; fatty acid esters, triglycerides; inorganic, plant, animal and synthetic waxes, silicones optionally containing functional groups selected from the group consisting of alcohol, amine and thiol functions; fluorosilicones; and perfluoro oils.

22. Process for the preparation of an oil-in-water emulsion according to claim 1 wherein the fluoro surfactant and the co-emulsifying agent are dispersed in the gelled aqueous phase, the perfluoropolyether, and the fatty alcohol are heated, and incorporated into the gelled aqueous phase with vigorous stirring.

23. Cosmetic or dermatological composition containing at least one emulsion according to claim 1.

24. Composition according to claim 23, which is in the form of a milk, a white care cream, an antisun cream, a tinted care cream, a foundation or a mascara.

* * * * *